(12) United States Patent
Abe et al.

(10) Patent No.: US 8,947,089 B2
(45) Date of Patent: Feb. 3, 2015

(54) MAGNETIC FIELD SHIMMING ADJUSTMENT: REDUCING MAGNETIC DISTRIBUTION ERRORS BY OBTAINING CURRENT POTENTIAL DISTRIBUTIONS OF MRI APPARATUS

(75) Inventors: Mitsushi Abe, Hitachinaka (JP); Ryuya Ando, Hitachi (JP); Takeshi Nakayama, Hitachinaka (JP)

(73) Assignees: Hitachi, Ltd., Tokyo (JP); Hitachi Medical Corporation, Tokyo (JP)

( * ) Notice: Subject to any disclaimer, the term of this patent is extended or adjusted under 35 U.S.C. 154(b) by 1034 days.

(21) Appl. No.: 12/991,495

(22) PCT Filed: May 8, 2009

(86) PCT No.: PCT/JP2009/058713
§ 371 (c)(1),
(2), (4) Date: Nov. 8, 2010

(87) PCT Pub. No.: WO2009/136643
PCT Pub. Date: Nov. 12, 2009

(65) Prior Publication Data
US 2011/0089943 A1    Apr. 21, 2011

(30) Foreign Application Priority Data

May 9, 2008    (JP) .................................. 2008-122843

(51) Int. Cl.
*G01R 33/3873*    (2006.01)
*G01R 33/3875*    (2006.01)
(Continued)

(52) U.S. Cl.
CPC ........ *G01R 33/3873* (2013.01); *G01R 33/3875* (2013.01); *G01R 33/389* (2013.01);
(Continued)

(58) Field of Classification Search
USPC .......................... 324/300–322; 600/407–435; 382/128–133; 702/65, 66; 703/2
See application file for complete search history.

(56) References Cited

U.S. PATENT DOCUMENTS 5,642,087 A * 6/1997 Crow ............................ 335/216
5,717,371 A * 2/1998 Crow ............................ 335/216
(Continued)

FOREIGN PATENT DOCUMENTS

JP    1-164356 A    6/1989
JP    2001-87245 A    4/2001
(Continued)

OTHER PUBLICATIONS

M. Abe et al., A new technique to optimize the coil winding path for the arbitrarily distributed magnetic field and application to a helical confinement system, Physics of Plasmas, vol. 10, No. 4, Apr. 2003, pp. 1022-1033.

*Primary Examiner* — Melissa Koval
*Assistant Examiner* — Tiffany Fetzner
(74) *Attorney, Agent, or Firm* — Mattingly & Malur, PC

(57) ABSTRACT

A measured error magnetic field distribution is divided into eigen-mode components obtained by a singular decomposition and iron piece arrangements corresponding to respective modes are combined and arranged on a shim-tray. An eigen-mode to be corrected is selected in accordance with an attainable magnetic field accuracy (homogeneity) and appropriateness of arranged volume of the iron pieces. Because the adjustment can be made with the attainable magnetic field accuracy (homogeneity) being known, an erroneous adjustment can also be known, and the adjustment is automatically done during repeated adjustments. As a result, an apparatus with a high accuracy can be provided. In addition, there is an advantageous effect of being able to detect a poor magnet earlier by checking the attainable homogeneity.

24 Claims, 10 Drawing Sheets

(51) Int. Cl.
*G01R 33/389* (2006.01)
*G01R 33/383* (2006.01)
*G01R 33/38* (2006.01)
*A61B 5/055* (2006.01)
*H01F 7/02* (2006.01)

(52) U.S. Cl.
CPC .............. *G01R 33/38* (2013.01); *G01R 33/383* (2013.01); *H01F 7/02* (2013.01); *A61B 5/055* (2013.01); *G01R 33/3806* (2013.01); *H01F 7/0284* (2013.01)
USPC ........... 324/319; 324/320; 324/318; 324/301; 324/307

(56) References Cited

U.S. PATENT DOCUMENTS

| | | | | |
|---|---|---|---|---|
| 5,748,063 | A * | 5/1998 | Crow | 335/299 |
| 6,078,872 | A * | 6/2000 | Carson et al. | 702/69 |
| 6,081,119 | A * | 6/2000 | Carson et al. | 324/307 |
| 6,181,137 | B1 | 1/2001 | Havens et al. | |
| 6,294,972 | B1 * | 9/2001 | Jesmanowicz et al. | 335/301 |
| 7,072,707 | B2 * | 7/2006 | Galloway et al. | 600/424 |
| 7,136,765 | B2 * | 11/2006 | Maier et al. | 702/65 |
| 7,253,624 | B2 * | 8/2007 | Ariyoshi | 324/320 |
| 7,565,189 | B2 * | 7/2009 | Mansfield et al. | 600/410 |
| 8,536,870 | B2 * | 9/2013 | Punchard et al. | 324/319 |
| 2002/0043975 | A1 | 4/2002 | Aoki | |
| 2004/0019274 | A1 * | 1/2004 | Galloway et al. | 600/425 |
| 2004/0036472 | A1 | 2/2004 | Goto | |
| 2005/0068030 | A1 * | 3/2005 | Mansfield et al. | 324/309 |
| 2006/0178849 | A1 * | 8/2006 | Maier et al. | 702/66 |
| 2010/0049482 | A1 * | 2/2010 | He et al. | 703/2 |
| 2011/0089943 | A1 * | 4/2011 | Abe et al. | 324/301 |
| 2011/0260727 | A1 * | 10/2011 | Punchard et al. | 324/318 |
| 2012/0235685 | A1 * | 9/2012 | Abe | 324/322 |
| 2012/0249137 | A1 * | 10/2012 | Witschey et al. | 324/309 |
| 2012/0268119 | A1 * | 10/2012 | Abe et al. | 324/307 |

FOREIGN PATENT DOCUMENTS

| | | |
|---|---|---|
| JP | 2002-177243 A | 6/2002 |
| JP | 2003-167941 A | 6/2003 |
| JP | 2004-81395 A | 3/2004 |

* cited by examiner

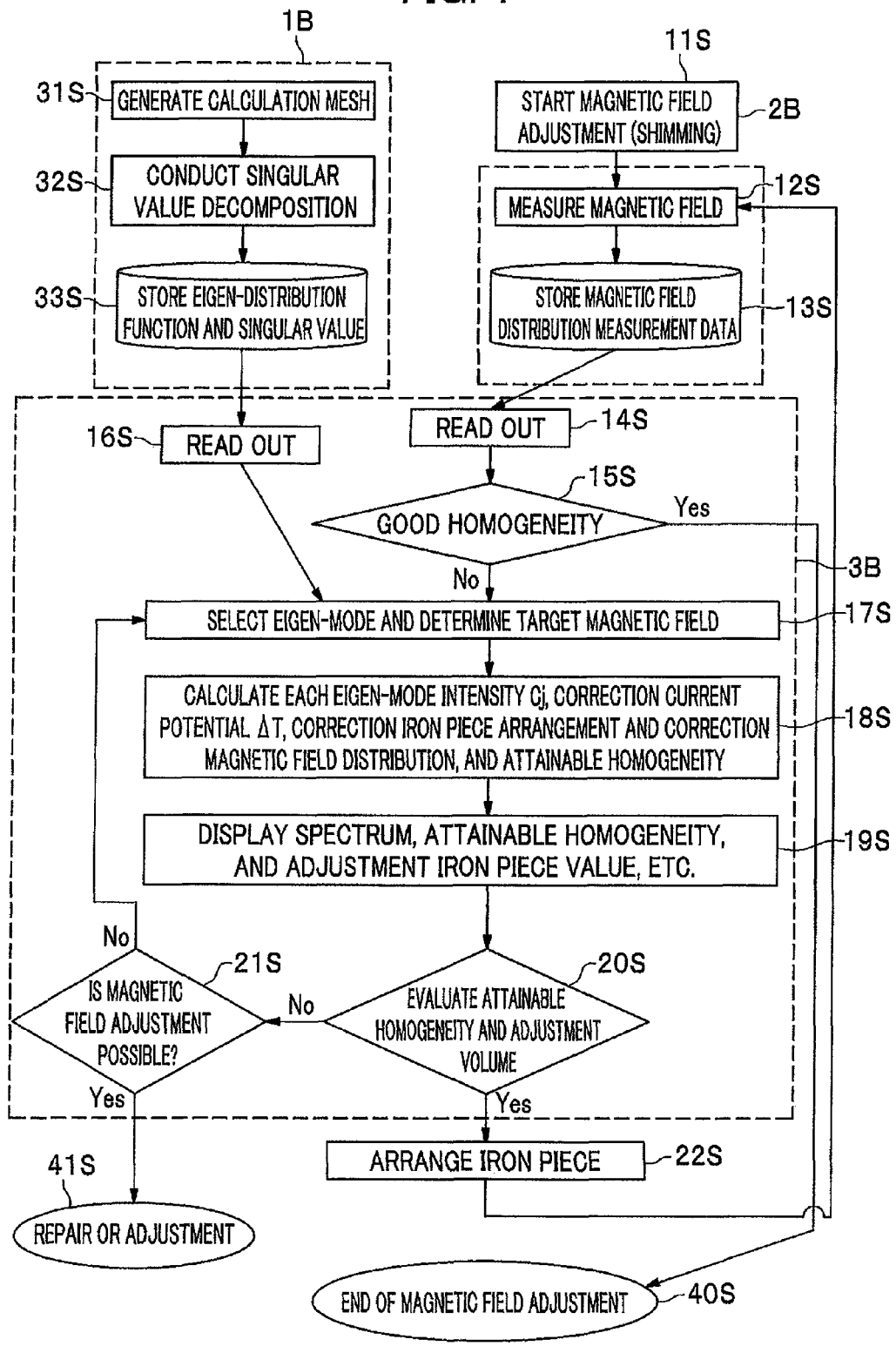

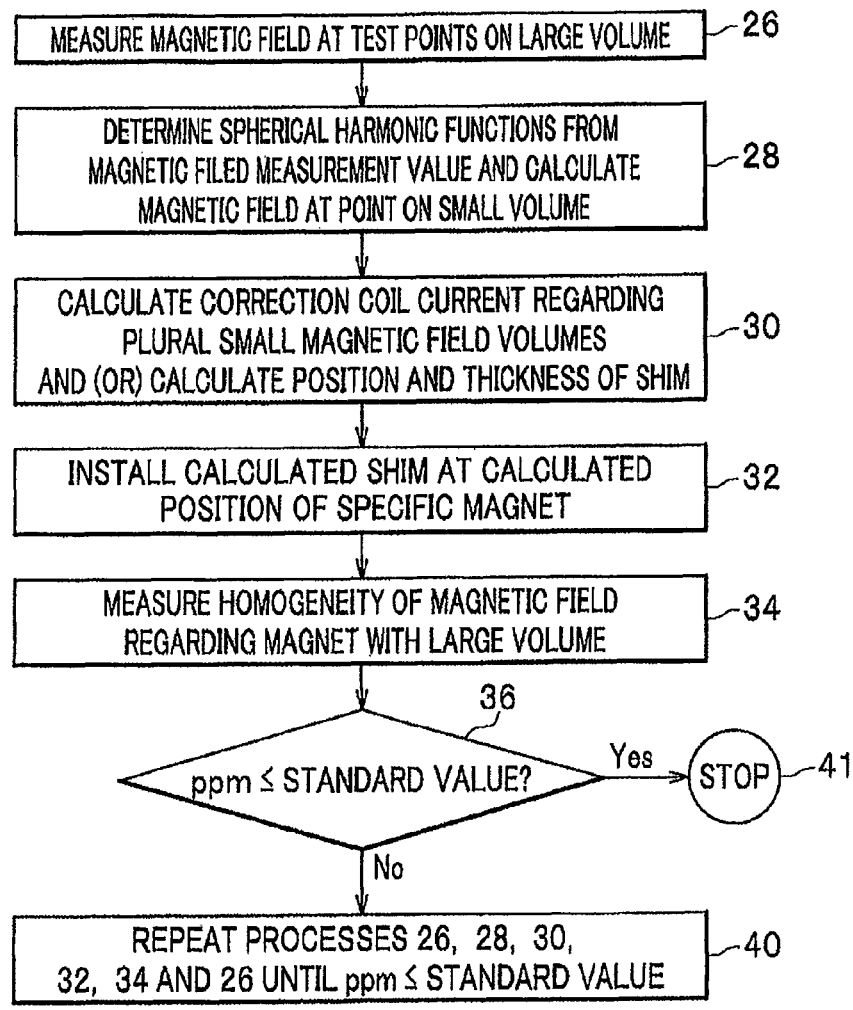
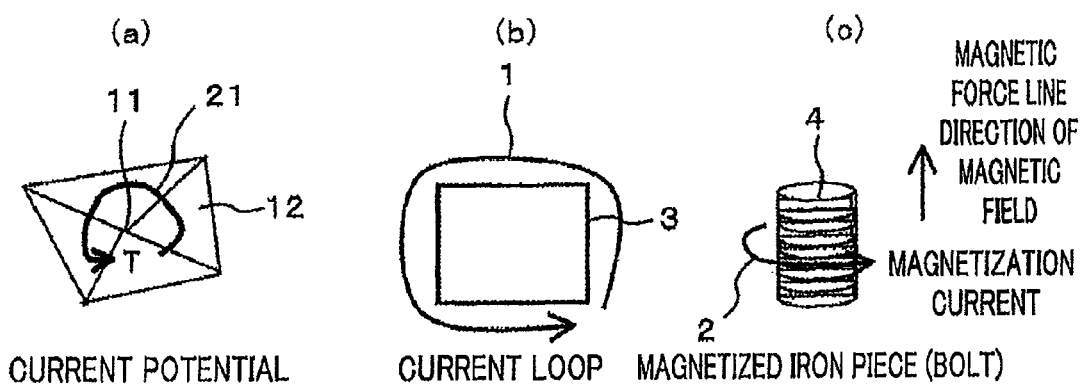

IRON VOLUME ∝ MAGNETIC MOMENT

MAGNETIC FIELD SHIMMING ADJUSTMENT: REDUCING MAGNETIC DISTRIBUTION ERRORS BY OBTAINING CURRENT POTENTIAL DISTRIBUTIONS OF MRI APPARATUS

TECHNICAL FIELD

The present invention relates to a superconducting magnet apparatus and a nuclear magnetic resonance tomographic apparatus (Magnetic Resonance Imaging).

BACKGROUND ART

In diagnosis using a nuclear magnetic resonance, a required accuracy in a magnetic intensity of the magnet system is such that variation of one millionth in magnetic intensity is considered to be a problem because a magnetic intensity corresponds to a diagnosis place. There are three types of magnetic fields in MRI apparatuses. That is:
(1) A magnetic field that is a constant in time base and uniform in space, and has an intensity of generally more than 0.1 to several teslas and a variation range of about several ppm within a space for imagining (a space of a sphere or an ellipsoid with a diameter of 30 to 40 cm);
(2) A magnetic field varying with a time constant of about one second or shorter and inclined in a space; and
(3) A magnetic field caused by a high frequency wave having a frequency (several MHz or higher) corresponding to the nuclear magnetic resonance.

Out of them, the magnetic field of (1) is required to be constant in time base and spatially have homogeneity in the magnetic intensity with an extremely high accuracy in the region where a tomographic imaging of a human body is done. "High accuracy" means that an accuracy with an order of one millionth, such as ±1.5 ppm, in an imaging space FOV (Field View) with a diameter of, for example, 40 cm. A magnetic field distribution of which homogeneity is required to be extremely high, requires adjustment for a magnetic field after production and excitation of a magnet. Generally, an error in magnetic field in production is 1000 times or more greater than the permissible error margin of the magnetic field demanded for a uniform magnetic field. Magnetic field adjustment (shimming) required when the apparatus is installed after production requires a magnetic field adjustment apparatus and a method with an extremely high accuracy because an error in magnetic field is reduced from hundreds ppm to several ppm.

There is a conventional method of shimming using a linear programming. For example, there is a method described by the patent document 1 or the patent document 2 and applied to actual apparatuses for adjustment. However, the linear programming has the following problems.
(1) The liner programming requires a long time period for calculation to conduct accurate calculations of the magnetic field.
(2) The linear programming requires such an accuracy that a magnetic field with a high accuracy is controlled in accordance with setting and variation of each iron piece and current.
(3) When an erroneous shimming operation is conducted, it is difficult to specify the place where the erroneous shimming operation is done, so that restoration requires a lot of work.

In addition, a problem occurs duet to adjusting the magnetic field distribution with spherical harmonic functions as shown in FIG. 2. FIG. 2 is a chart showing an example of a conventional magnetic field adjustment method using the spherical harmonic functions (Patent Document 1).

The spherical harmonic functions are orthogonal on a spherical surface to form a base, but when a magnetic field with a spherical function distribution having a high accuracy is tried to generate, a fine adjustment for a magnetic adjustment mechanism is required because there is a mutual interference in the magnetic field adjustment mechanism and on a magnetic field evaluation surface of an aspheric surface. For example, a homogeneous magnetic field distribution is a distribution having the lowest-numbered spherical harmonic functions. However, it is impossible to actually generate this distribution accurately unless using a magnetic adjustment mechanism which perfectly encloses a magnetic adjustment region. Accordingly, the MRI of the prior art has no such a magnetic adjustment mechanism.

PRIOR ART TECHNICAL DOCUMENTS

Patent Documents

Patent Document 1: JP 2001-87245
Patent Document 2: JP 2003-167941

Non-Patent Document

Non-Patent Document 1: M. ABE, T. NAKAYAMA, S. OKAMURA, K. MATSUOKA, "A new technique to optimize coil winding path for the arbitrarily distributed magnetic field and application to a helical confinement system", Phys. Plasmas. Vol. 10 No. 4 (2003)1022.

DISCLOSURE OF THE INVENTION

Summary of Invention

Problem to be Solved by Invention

An object of the present invention is to provide a method and an apparatus in which the above-mentioned problem can be solved and adjustment can be surely completed with confirming a progress status of the adjustment and a prospect as to which degree the final erroneous magnetic field can be reduced to. Another object of the present invention is to provide a method including a function capable of easily, automatically, performing correction to quickly complete the adjustment even if the operation is erroneously done and to provide an apparatus with the method, wherein the apparatus displays an indication of the magnetic field adjustment method.

Measures for Solving the Problem

As a method of obtaining a current distribution for a target magnetic field on a given surface such as a curved surface or a flat surface, there is a method with current potential described in a paper (Non-patent document 1). This calculation method is named DUCAS in the paper. The magnetic field adjustment is performed by applying this DUCAS method, particularly, by applying the idea of a current potential and a singular value decomposition used in the method.

In DUCAS in the non-patent document 1, a magnetic field distribution to be entered as an error magnetic field to be corrected is a difference from a magnetic field distribution calculated using the current potential, etc. which are associated with assumption of the target magnetic field determined in a plasma confinement theory, i.e., values obtained by a numeric value calculation. On the other hand, because the present invention targeted on an actual apparatus, a difference between a target magnetic field and a measured magnetic field is defined as an error magnetic field and a lot of measurement magnetic field at a lot of points are dealt to grasp an error magnetic field distribution.

In addition, in the non-patent document 1, a distribution of a current potential T is obtained, in which case a current density vector $\vec{j}$ is a vector product of current potential $\vec{T}$ and a normal vector on a surface, and thus a current is obtained from $(\nabla \vec{T}) \times \vec{n}$, a counter line of $\vec{T}$ is shown as line currents or in a coil shape. However, in the present invention, it is a magnetic moment distribution or an iron piece density distribution.

Advantageous Effect of the Present Invention

According to the present invention, an MRI apparatus that generates a magnetic field with a high accuracy can be produced at a low cost.

BRIEF DESCRIPTION OF DRAWINGS

FIG. 1 illustrates a magnetic field adjustment flowchart of a preferred embodiment of the present invention.

FIG. 2 illustrates a conventional shimming flowchart.

FIG. 3 is illustrations of an idea of conversion between current potential and a magnetized iron piece volume for the magnetic field adjustment which is necessary for correcting the magnetic field according to the preferred embodiment of the present invention.

BEST MODE FOR CARRYING OUT THE INVENTION

Figure 4:
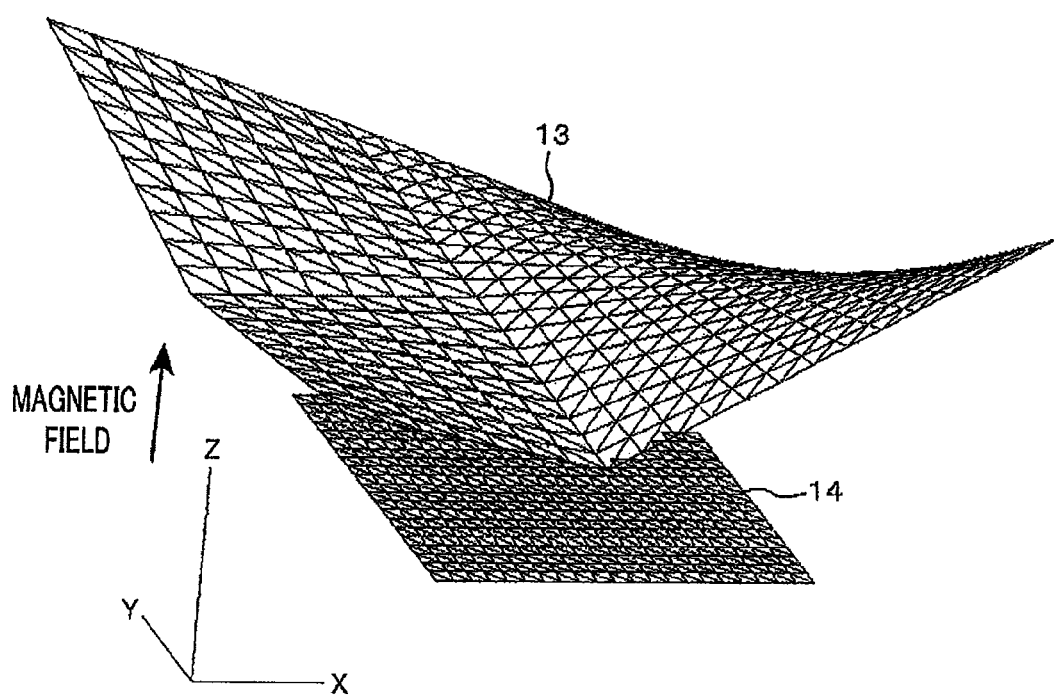
FIG. 4 is a chart of an example of a general system of a calculation system used in a preferred embodiment of the present invention.

With reference to drawings will be described embodiments of the present invention.

FIG. 3 shows equivalence among a current potential, a current loop by a small coil, and a magnetized iron piece.

FIG. 3 (a) shows a current 21 by a finite element 12, a node 11, and a current potential T for calculation. FIG. 3 (b) shows a magnetic moment generation by the current 1 flowing through a small coil 3. FIG. 3 (c) shows a magnetic moment by a magnetization current 2 by an iron piece 4. As shown in FIG. 3 (a), if the current potential T has a certain value at a node 11, this can be understood such that the current 21 rotationally flow between nodes around the current 21. In other words, this is equivalent to a situation in which the current 1 flows through the current loop of the small coil 3 in FIG. 3(b). In addition, this is equivalent to a situation shown on the right side where the magnetization current 2 which is $j_m$ (A/m) flowing on a surface of the magnetized iron piece 4. In other words, the current potential value T used for expressing a current distribution by DUCAS has a dimension of [A] as unit. However the current potential value T can also be considered to have a dimension of [A] because of a density [$1/m^2$] of the magnetic moment [$Am^2$].

On the other hand, the iron piece 4 sufficiently magnetized has a magnetic moment proportional to a volume thereof because the magnetic moment is in proportion to a product of an area surrounded by the magnetization current and a length in a direction of the magnetic force line. In other words, the current potential T when the magnetic field adjustment is done, is a quantity proportional to a density of the iron piece 4 [weight per a unit area, i.e., $g/m^2$ or a volume $cc/cm^2$]. This characteristic is used, and an eigen-distribution function and a singular value, obtained by the singular value decomposition, used in DUCAS in place of the spherical harmonic functions which is a conventional method, are used.

According to this, an apparatus is provided which conducts, using DUCAS, a support calculation for adjusting a magnetic field in which a magnetic field generating apparatus is a target and which displays an arrangement of the iron pieces for the adjustment or an arrangement of the magnetic moment. An operator can do adjustment toward a target magnetic field distribution by advancing the adjustment in accordance with the display.

The present invention allows a given magnetic field distribution to be a target magnetic field. However, argument is mainly made with assuming that the target magnetic field is uniformly homogeneous. However, whether the target magnetic field has a distribution does not affect the argument below. This is simply provided to make it easy to understand the argument.

The error magnetic field $B_{err}(\vec{r})$ is a function of position, but is considered to be a combination of the eigen distribution functions in the present invention. That is, the error magnetic field $B_{err}(\vec{r})$ is given by:

[Formula 1]

$$B_{err}(\vec{r}) = \Sigma C_m \psi_m(\vec{r}) \quad (1)$$

In the conventional method, Legendre polynomial or spherical harmonic functions is used. In the present invention, a distribution function by the singular value decomposition is used. Will be described a way of determining the function $\psi_m$ to be summed and its coefficient $C_m$ more specifically.

In the argument of the present invention, a system shown in FIG. 4 is considered as a general system. FIG. 4 shows a calculation system of the present embodiment. It is formed with a potential evaluation plane 13 and a set 14 of magnetic field measurement evaluation nodes. Generally, there may be a case where a plurality of current potential evaluation planes 13 exist, but the argument is made with assumption that there is one current potential evaluation plane 13 here. In addition, the magnetic field evaluation nodes do not always form a plane, but the magnetic field evaluation nodes are shown as points on a plane.

A measurement point j has three-dimensional magnetic field components $B_{xj}$, $B_{yj}$, $B_{zj}$. In the measurement at a point, the measured magnetic field components are shown with the position and a unit vector p defined at the position. There may be a case where there are three pieces of data although the number of points in a space is one.

In addition, when a homogeneous magnetic field is obtained like the MRI apparatus, only main component in an axial direction of the magnetic field is made constant. This is because although it is important that an intensity of the magnetic field is constant in the MRI, the main component of the magnetic field is approximately equal to an intensity of the magnetic field, because components other than the main component are very weak.

In the error magnetic field that is a difference between the measured values and the target magnetic field, there are a plurality of pieces of measured data, the whole of the pieces of the measured vector being represented as $\vec{B}_e$. The error magnetic field $B_e$ is a difference between the measured magnetic field $B_m$ and a magnetic field intensity $Bt_g$ for adjustment to have a homogeneous magnetic field.

An error magnetic field corresponding to the measurement point j is $\vec{B}_e$ having components of $B_{ej}$ and is given by Eq. (2) as follows:

[Formula 2]

$$B_{ej} = B_{tg} - B_{mj} \quad (2)$$

A general system, to which singular value decomposition is applied, is as shown in FIG. 4. There is a region of evaluation nodes of the magnetic field, and the magnetic field is measured at the evaluation nodes. The iron pieces for adjusting the magnetic field are arranged on a CSS plane. The plane is called a shim-tray in the MRI.

Will be described a relation between an iron density and error magnetic field correction. The plane is divided into triangle elements and a current potential is assigned to the node. This is described in the non-patent document 1. A relation between a magnetic field vector having the measurement data as an element at the evaluation nodes of the magnetic field and the current potential vector having the current potential on the CCS plane as an element is given by Eq. (3) as follows:

[Formula 3]

$$\vec{B} = \vec{\vec{A}} \cdot \vec{T} \quad (3)$$

Eq. (3) is an equation representing a response of the magnetic field at the evaluation node of the magnetic field from a vector $\vec{T}$ having a current potential value at a node on a current plane as an element. Matrix $\vec{\vec{A}}$ is m (the number of the evaluation nodes of the magnetic field) row and n (the number of nodes) columns.

A set of an eigen-distribution function of a magnetic field distribution and a current potential is obtained by effecting the singular value decomposition on a response matrix A' to the magnetic field evaluation node from a current potential at an isolated node obtained by adding a constraint of a node to the matrix A. That is, it is a set of eigen-distributions $\vec{u}_1$, $\vec{u}_2$, $\vec{u}_3$ which is a base of the magnetic field distribution and eigen-distributions $\vec{v}_1$, $\vec{v}_2$, $\vec{v}_3$ which is a base of the current potential, and there is a relation given by Eq. (4) between $\vec{u}_j$ and $\vec{v}_j$.

[Formula 4]

$$\lambda_j \vec{u}_j = \vec{\vec{A}} \cdot \vec{v}_j \quad (4)$$

Here, $\lambda_j$ is a singular value. Further, the subscript j is the number of order in which a number is assigned to each eigen distribution in magnitude order of the singular values. Each of base vectors indicating the current potential distribution and the magnetic field distribution corresponds to one number. It is assumed that two base vectors relating one number and one singular value are referred together to as one eigen-mode. Further, the ordinal number j is a number of order of the eigen-mode.

It can be said that a low-numbered eigen-mode which has a large singular value can generate a large magnetic field intensity as it is understood that a magnetic field intensity per a unit current potential distribution $v_j$ is $\lambda_j u_j$. On the other hand, when a current potential is varied in an eigen-mode having a small singular value, a change in a distribution of the magnetic field is small. This characteristic, which will be described later, will play an important role in this magnetic field adjustment method. As the distribution function defined by Eq. (1) the distribution of an eigen vector obtained by the singular value decomposition is used.

Will be described a correction method or adjustment method (reduction of the error magnetic field by shimming) of the error magnetic field corresponding to the eigen-mode having an order number j. A coefficient $D_j$ indicating what times as large as the base current potential distribution $\vec{v}_j$ can be obtained from the error magnetic field distribution. The magnitude can be obtained from Eqs. (5) and (6).

[Formula 5]

$$C_j = \vec{B}_e \cdot \vec{u}_j \quad (5)$$

$$D_j = -C_j / \lambda_j \quad (6)$$

In other words, an error magnetic field of j-$^{th}$ eigen-distribution can be perfectly corrected by giving a current potential distribution $D_j \vec{v}_j$.

Next, will be described a relation between the current potential and an iron piece density. The iron piece can be replaced with a magnetic moment in consideration of a magnetization current on a surface thereof. A magnetization current $j_m$ (A/m) on a surface of the iron piece is given by Eq. (7).

[Formula 6]

$$j_m = M / \mu_0 \quad (7)$$

Here, M means a magnetization (T). When the iron piece is in a saturation status, M is about 2.1 T. Accordingly, $j_m$ is about $1.7 \times 10^6$ A/m. Accordingly, iron having a volume of one cubic meter has a magnetic moment of about $1.7 \times 10^6$ Am$^2$ (170 Acm$^2$/1 cc). Because this value depends on a kind of a magnet and particularly on the magnetic field intensity, it necessary to make consideration for each case. However, in the magnets having a magnetic intensity exceeding approximately 1 T, it is natural that the iron piece is magnetized in a status near saturation. In this status, the magnetic moment of iron is proportion to a volume of the iron piece.

In this conversion, in order to cancel out the error magnetic field of j-$^{th}$ eigen-mode, an iron piece is arranged with a volume density (m=m$^3$/m$^2$) corresponding to a component $d_{jk}$ of $\vec{d}_j$ (an iron volume at k-$^{th}$ iron piece correction node corresponding to j-$^{th}$ eigen distribution function). Further, in a case where the magnetic field is corrected by arranging a current given by $(\nabla \vec{T}) \times \vec{n}$ in which is vector $\vec{j}$ is a vector product of the current potential $\vec{T}$ and a normal vector on a surface.

[Formula 7]

$$\vec{d}_j = -\vec{v}_j C_j / (\lambda_j j_m) \quad (8)$$

The above-mentioned method is a basic method of correction. This is correction of components by the singular distribution ($\vec{u}_j$) of an error magnetic field. The correction according to the present invention features that the distribution functions ($\vec{v}_j$, $\vec{u}_j$) are basis, respectively, and correspond to each other one by one. To correct one of the eigen-distribution components, a distribution function of only on adjusting means is adjusted.

Even in the method according to the present invention, there are many eigen-distribution functions of the error magnetic field to be corrected. The above-mentioned method is expanded to a selecting method of the eigen-mode to be corrected from many eigen-modes and the correcting method. A basic way of considering this has the following items:

(1) It is selected from the eigen-modes which can correct a large magnetic field with a small current potential (i.e., with a small volume of iron piece). An index used for this selection is a singular value $\lambda_j$. Because the singular value is a magnetic intensity per a unit current potential for each eigen-distribution in this calculation system, the singular distribution having a small singular value is not selected. In other words, it is also can be said that the singular value is a value which is proportional to a magnetic field intensity per a unit iron volume. Generally, because it is desired to generate a homogeneous magnetic intensity with a small volume, an eigen distribution having a large singular value is used for adjustment.

(2) One having a small component intensity of the eigen magnetic field distribution included in a measurement magnetic field is negligible. If a component intensity calculated in an inner product (Eq. 5) is an intensity sufficiently smaller than an allowed error magnetic field at a target homogeneous magnetic level, further correction is not necessary. When the eigen component has a small component intensity although the eigen distribution has a large singular value, it has a large singular value, it is not selected because it is not necessary to be used in shimming.

(3) An eigen-distribution function is selected individually which the operator particularly determines to be necessary for correction, and it is corrected with an intensity obtained by the inner product or an intentionally determined intensity. For example, in a case where a locally large error magnetic field occurs because peaks of the error magnetic field distributions are overlapped, correction by correction of intentionally decreasing peaks is conducted by selecting a proper eigen-distribution function with a proper magnitude.

(4) A homogeneity (attainable homogeneity) after the current potential component of the selected eigen-distribution function is corrected, is obtained and it is determined whether the selection of the eigen-distribution function is proper. If the attainable homogeneity is insufficient, the selection of the eigen-distribution function is considered again. The homogeneity is a difference in magnetic field intensity between the maximum and the minimum among the plurality of measurement points in the magnetic field evaluation region, in other words, the homogeneity indicates a ratio of the peak-to-peak difference in the error magnetic field with respect to an average magnetic field and is generally argued at an order of one millionth (ppm) in the MRI.

(5) When the target magnetic field is changed, because an intensity of each eigen-distribution included in the error magnetic field and an intensity of the magnetic field left as a residual difference, i.e., the homogeneity, changes, it is necessary to consider the target magnetic field in selecting the eigen-distribution.

(6) Adjustment is carried out by repeating operation from several to tens times. That is, an accuracy of the magnetic field is increased because an accuracy of adjustment mechanism is generally coarser than the accuracy of the magnetic field to be a target. For example, in shimming in the MRI, it is necessary to conduct the magnetic field adjustment with an accuracy of one micro tesla, however, the error magnetic field before shimming is around several milli-teslas. When this is adjusted at one trial, it is required to control the iron piece to be arranged for the adjustment in volume at a fine accuracy equal to or smaller than $1/1000$. Then, according to the present invention, at the first adjustment, the error magnetic field is decreased at an accuracy in control volume equal to or smaller than approximately $1/10$ and the error magnetic field is decreased in accordance with the number of times of adjustment. Accordingly, a relative ratio with the final magnetic field accuracy is decreased to provide a sufficient final accuracy in the magnetic field even with a volume control of equal to or lower than $1/10$.

Next will be described a relationship between the iron piece arrangement and the above-mentioned description in consideration of the case where the shimming is conducted with the iron piece. A correction quantity $\vec{D}$ corresponding to the selected eigen-distribution is a sum of correction volumes $\vec{d}_j$ by the respective eigen-distribution functions and is given by Eq. (9).

[Formula 8]

$$\vec{D} = \Sigma \vec{d}_j = \Sigma - \vec{v}_j C_j / (\lambda_j j_m) \quad (9)$$

where the sum of $\Sigma$ is conducted with respect to the eigen-functions selected. It is easy to predict through calculation how the magnetic field distribution in the imaging region after conduction of the correction becomes.

There is one method in which it can be obtained from functions of the eigen-distribution functions of the magnetic field distribution. It is given by Eq. (10).

[Formula 9]

$$\vec{B}_{shim} = \vec{B}_e - \Sigma C_j \vec{u}_j \quad (10)$$

where the sum $\Sigma$ is conducted for the selected eigen-distribution functions.

The other is a method reconstructed with the current potential reconstructed. A correction $\Delta \vec{T}$ of the current potential in Eq. (10) is given by Eq. (11), and the error magnetic field distribution $\vec{B}_{shim}$ is given by Eq. (12).

[Formula 10]

$$\Delta \vec{T} = \Sigma - \vec{v}_j C_j / \lambda_j \quad (11)$$

$$\vec{B}_{shim} = \vec{B}_e - \tilde{A} \Delta \vec{T} \quad (12)$$

These two methods provide the same calculation results. Here, the sum $\Sigma$ is conducted for the selected eigen-distribution functions. By the calculation method, the attainable homogeneity after the magnetic field adjustment is predicted to determine whether the magnetic field adjustment advances in a target accuracy of the magnetic field adjustment.

The determination is carried out with reference to the iron volume necessary for shimming in addition to the attainable homogeneity. If an excessive iron piece is necessary, the selection of the eigen-distribution functions is considered again. If calculation of all selections provides that an excess volume of the iron pieces is necessary, it can be determined as a magnet with poor magnetic design or poor manufacturing.

This function is applicable to:
(a) quality assurance of magnet product; and
(b) consideration whether a design of arrangement of electromagnetic forces is proper and whether reconsideration of arrangement is necessary or not.

Operations of the improved items in the present invention will be described.

In the selection of the Eigen-mode in the item of (1) is selected to correct the error magnetic field with respect to low-numbered eigen-distribution functions. A low-numbered distribution function is selected within a range of compensating correction for the magnetic field with a small quantities of iron piece. Even if only low-numbered distribution functions are selected, generally, tens to hundreds eigen-distribution functions are selected. By correcting the magnetic field in accordance with the arrangement of the iron piece (current potential) arrangement with the eigen-distribution functions, correction can be done without a large affection or a new error magnetic field to the not-selected eigen-distribution. This provides an advantageous effect in avoiding disturbance of high-order components (eigen-distribution numbered with high order) which were not selected. In other words, when the magnetic field adjustment is conducted, the operation does not become complicated because the non-selected high order eigen-distribution becomes disturbed.

The low-numbered eigen-distribution functions selected by the singular value decomposition can be corrected with a low volume of the iron piece, but a larger volume is necessary to vary the high-numbered eigen-distribution functions. The reason why the high-numbered part is not disturbed is that a large value of the iron piece is necessary for changing the high-numbered eigen-distribution functions in addition to that the distribution is orthogonal. More specifically, correction for the low-numbered distribution function which needs a small volume of iron piece does not result in change in an intensity of a high-numbered component even if the arrangement is disturbed regarding the error. Also for this reason, the eigen-distributions are selected from the low-numbered eigen-distributions.

In addition, because a magnetic field of low-numbered components that can be corrected are large in proportion to the singular value, the magnetic field adjustment, i.e., shimming, can be done with a small volume of the iron piece efficiently.

In the item (2), the eigen-distribution function for which the correction is not necessary is not corrected. However, if it is included in the adjustment volume by selection, because a magnitude of adjustment volume is small, it doe not disturb the high-numbered components as mentioned above, and thus there is no problem.

The item (3) is adjustment of selection between the iron arrangement amount and the magnetic field distribution. In a case where the magnetic field is corrected with only iron piece, there may be a case where an adjustment by a negative volume of iron piece, i.e., removing the iron piece, is difficult to be conducted. On the other hand, arrangement of the iron piece for a high-numbered distribution generates a small magnetic field. In other words, arranging an iron piece for a high-number component provides a space for removing an iron piece in correction for the low order. In addition, if the homogeneity is defined within a range from a positive peak value to a negative peak value, there may be a case where an indication of the homogeneity becomes worse particularly at the peak part concentrically. In this case, a proper correction component is intentionally added. This allows the homogeneity to reach the target.

The item (4) enables checking whether the magnetic field can be adjusted at a target accuracy. When the magnetic field is corrected with respect to the selected eigen-distribution functions, it is necessary that the homogeneity finally reaches a target by repeating the correction. This method provides prediction as to what homogeneity can be obtained by the calculation method mentioned above. In accordance with the prediction, it is determined whether the selection of the eigen-distribution functions should be changed. In a case where only low value of the homogeneity can be obtained, it can be determined that the quality is problematic because there is a problem in production. The problem in quality may frequently occur at the high-numbered components, in which case it is difficult to conduct correction. On the other hand, in the method of the present invention in which the components are divided by the singular value decomposition, it is easy to discover a problem occurring at the high-numbered eigen-modes.

The item (5) is to select a setting intensity of the magnetic field intensity to be homogeneous. The eigen-distribution functions are selected while the target magnetic field is changed, and an attainable homogeneity and the volume of the iron piece are checked. Then, a target magnetic field is selected to have a good homogeneity and an easy arrangement of the iron piece. Easy arrangement of the iron piece is not that the volume is small, but that an arrangement allows a relative-low-number distribution functions to be sufficiently corrected and has no region where the iron piece having a negative volume value is arranged.

The item (6) completes the magnetic field adjustment by repeating the operation from the measurement to the arrangement of the iron piece. Depending on a geometrical arrangement subject to the magnetic field adjustment, there is a difference in a magnitude of the singular value selected of about four figures between the selected low-numbered singular value and the selected high-number singular value at the maximum. In other words, adjustment varies in accordance with the selection of the eigen-distribution functions from an adjustment in which a volume of about 100 cc is handled in the magnetic adjustment to an adjustment in which a volume of 0.01 cc is handled. On the other hand, it is not easy to control the adjustment with an accuracy in which 1/10 of iron piece is handled. Then, the adjustment is repeatedly done to correct the residual error in the magnetic field, so that even if every adjustment has only 1/10 of accuracy, a final accuracy can reach a good homogeneity. During repeating, at a first stage, eigen-distributions up to high-numbered eigen-distributions are selected to do an adjustment for a larger volume and then, an upper limit of the order is gradually decreased. When the number of the order is decreased, it is confirmed that a high-numbered part has been sufficiently corrected. In addition, as the number of order is decreased, the volume as the result of the calculation for correction decreases. Accordingly, the adjustment accuracy of about one tenth of the volume will increase.

The magnetic field adjustment is conducted repeatedly. Here, as described with respect to the item (2), the high-numbered eigen-modes not selected are not disturbed. Accordingly, the homogeneity predicted does not vary during repeating.

As mentioned above, according to the method of the present invention based on the eigen-distribution functions obtained from the singular value decomposition of the response matrix from the current potential on the shim-tray to magnetic field intensities at magnetic field evaluation nodes placed on the imaging region, the target magnetic field homogeneity can be obtained with a low adjustment volume for the error magnetic field in which the magnetic field after adjustment is being predicted. Shimming operation should be repeated. In addition, during a repeating operation, when the shimming is conducted, particularly for high-numbered distribution, there is a case where the homogeneity apparently becomes worse because error magnetic field components corresponding to a low order distribution functions increases. On the other hand, the method also has an advantageous effect in that it is confirmed how the magnetic field adjustment advances by confirming component intensities of the eigen distribution functions, which results in that components on the side of high orders selected are corrected. This is advantageous to the operator in confirming appropriateness of the operation. In addition, there is an advantageous effect in that the adjustment is advanced with easiness feeling because it is confirmed that the magnetic field adjustment for a manufacturing error up to the target accuracy is not impossible because the homogeneity attainable at an end of adjustment can be grasped.

First Embodiment

Figure 5:
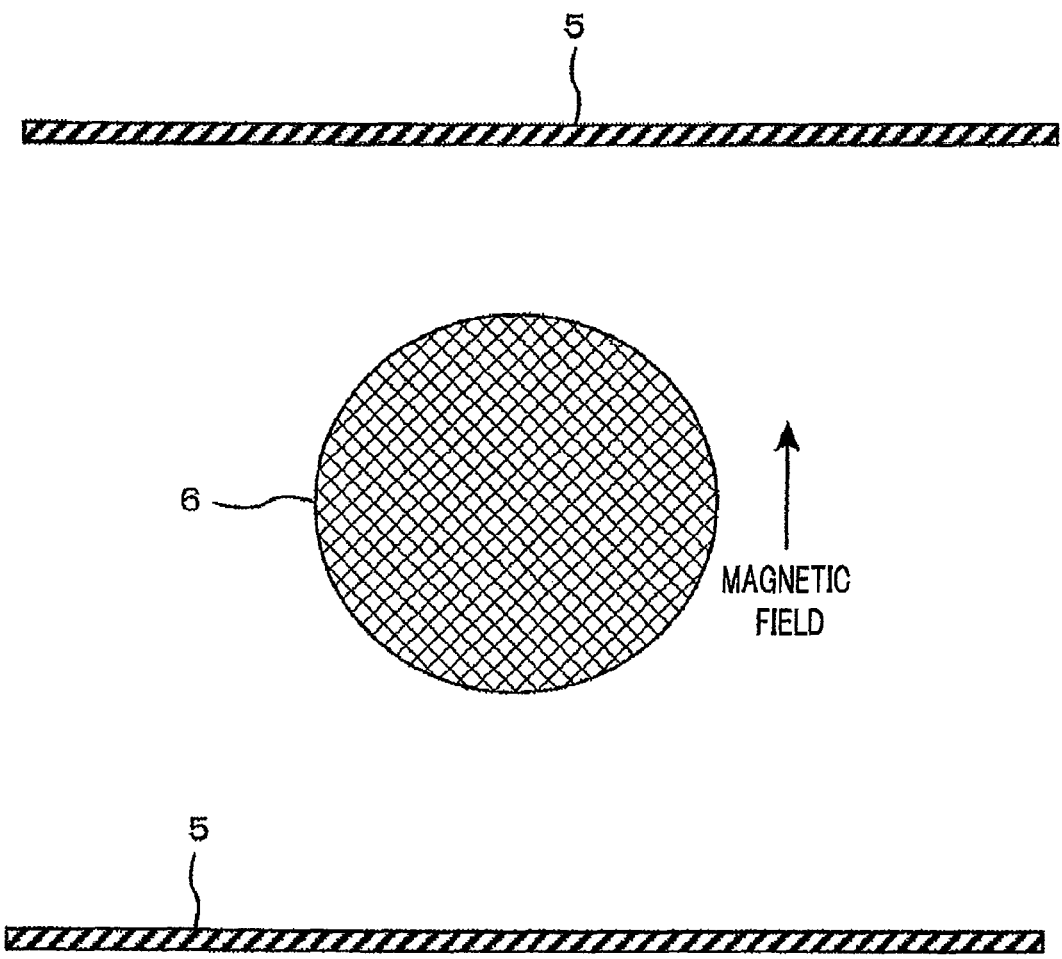
FIG. 5 illustrates an arrangement illustration of the magnetic adjustment mechanism for an MRI magnet used for magnetic field adjustment of the preferred embodiment of the present invention.

Will be described a first embodiment. Application to the magnetic field adjustment (shimming) in an open type MRI apparatus having a vertical magnetic field will be described as the first embodiment. FIG. 5 shows a system of the magnetic field adjustment (shimming) for a magnetic field generated by a magnet of the MRI apparatus in FIG. 5. There is a space (magnetic field measurement evaluation region) 6. The magnetic field distribution at magnetic field evaluation node on a surface thereof or an inside surface thereof is adjusted (shimmed) to be homogeneous. FIG. 1 shows a flowchart of shimming for adjusting the magnetic field distribution in the first embodiment. This is an embodiment where this is applied to the magnetic field adjustment in an imaging region of the open and vertical magnetic field type of MRI apparatus. An intensity of magnetic field component is vertical to a ground surface. There are magnetic field adjusting mechanism planes (shim-trays) 5 above and below the imaging region, and iron pieces 4 are arranged on the magnetic field adjusting mechanism planes.

Figure 6:
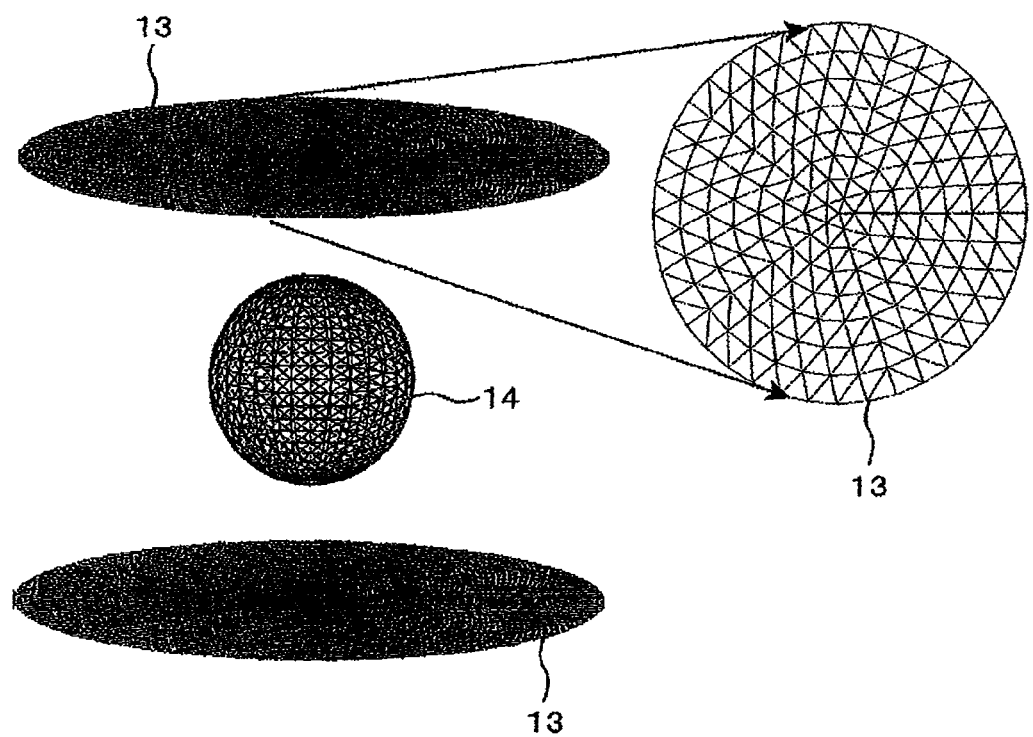
FIG. 6 illustrates an illustration of a calculation model for applying the present invention to the magnetic field adjustment shown in FIG. 5.

FIG. 6 shows an example of mesh generation when the first embodiment is applied to the shimming in the MRI apparatus. In the first embodiment, there are hundreds of magnetic field measurement nodes are arranged as a set 14 of the magnetic field measurement nodes on a surface of a sphere. Circular disk planes above and below the sphere are calculation models of the planes where the iron piece(s) 4 are arranged when shimming is carried out, i.e., current potential evaluation surfaces 13. As roughly shown by finite elements on the right side of the drawing, a system of finite element calculation including triangle elements with nodes on the plane is formed.

A pre-calculation part 1B inside a broken line in FIG. 1 is calculated before a shimming work process. It includes a singular value decomposition calculation step 32S, a calculation mesh generation step 31S, a storing step 33S of the eigen-distribution function and the singular value as the result of the singular value decomposition. This part is a pre-calculation part 1B including the singular value decomposition of a response matrix A from nodes corresponding to current potential values at thousands of points to magnetic field measuring points of hundreds in the imaging region, and thus needs a relative long calculation period. Therefore, the eigen-distribution functions are calculated for shimming through the calculation system matched to a system of magnet to shorten a calculation time period of the shimming work process.

The data previously calculated is stored in a storage region of a computer by the storing step 33S. The data is read out (reading out step 16S for the singular value decomposition result) as needed, and used. In other words, during calculation, the eigen-distribution functions more than several, the same number of base vector groups which are distribution functions on a current plane, and the same number of singular values which are conversion information therebetween in magnitude, are combined and stored.

After a certain time elapses after excitation of the magnet, a step of starting the magnetic field adjustment (shimming) 11S is done. The magnetic field adjustment work process is carried out in accordance with the flowchart in FIG. 1. A magnetic field measurement step 12S is conducted. After a magnetic field distribution data storing step 13S and a magnetic field data reading step 14S, it is determined whether the homogeneity is good in a magnetic field homogeneity determining step 15S. If the homogeneity is sufficient, the shimming is not necessary, the work process progress to a magnetic field adjustment completion step 40S. This can occur in a case where an apparatus used with a sufficient homogeneity is re-excited after de-magnetization on maintenance. On the other side, in a case of a new magnet, due to a manufacturing error, the homogeneity is from about hundreds to thousands ppm. In this case, it is determined that the magnetic field adjustment (shimming) is necessary.

Then, the process moves to a step S17 of eigen-mode selection and determination of a target magnetic field. In the next step 18S, an eigen-mode is selected, and Eqs. (1) to (12) for each eigen-mode intensity $C_j$, adjustment current potential $\Delta \vec{T}$, adjustment iron piece arrangement, and adjustment magnetic field distribution, and attainable homogeneity, are calculated for the selected eigen-mode.

Next is a display step 19S for determining appropriateness of selecting the eigen-mode. A calculation result in the step 18S is displayed to determine appropriateness of selecting the eigen-mode. There are two display modes. One is shown in FIG. 7 and the other is shown in FIG. 8.

Figure 7:
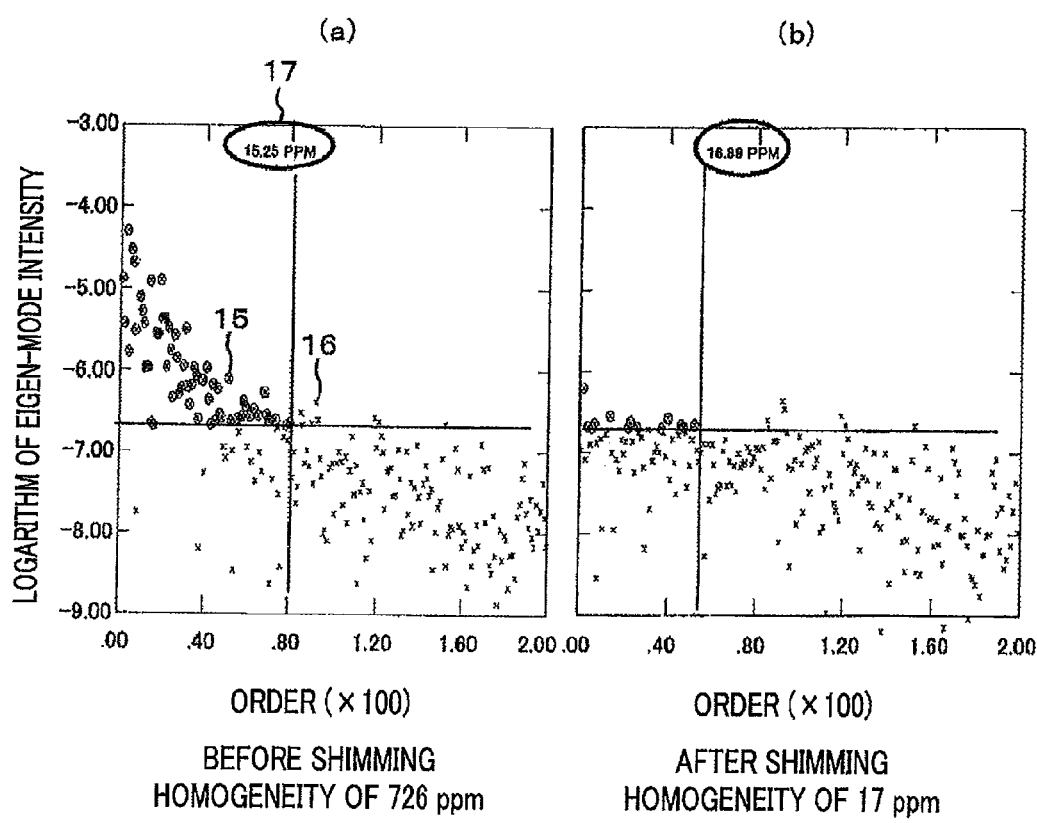
FIG. 7 illustrates charts showing spectrums of magnetic field distribution together with an attainable homogeneity, in which (a) illustrates the spectrum before shimming and (b) illustrates the spectrum after shimming.
Figure 8:
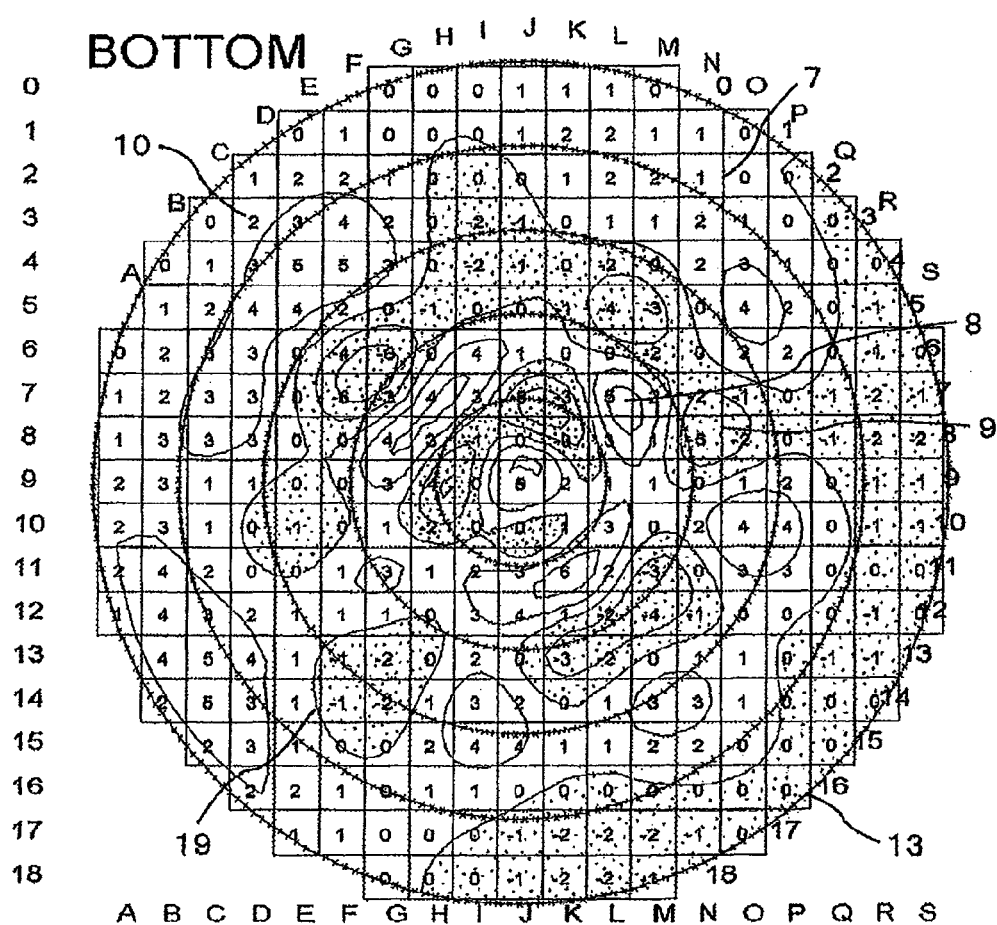
FIG. 8 illustrates a display example of iron volume arrangement for adjusting a magnetic field correction on a shim-tray together with the current potential contour line according to the present invention.

FIG. 7 is a chart showing eigen-mode intensity along a vertical axis and the number of order of the eigen-mode, of the magnetic field included in the error magnetic field obtained by an equation such as Eq. (5) and called spectrums. The vertical axis is shown in a logarithm scale. FIG. 7 also shows a range of selecting an eigen-mode and the attainable homogeneity. In addition, FIG. 8 shows a display example of an iron piece arrangement volume for shimming work process with current potential contour lines.

The detail of calculation explained in this example is shown in FIGS. 5 and 6. It is assumed that magnetic field evaluation nodes are on a surface having a diameter of 40 cm. A target is to make the error magnetic field equal to or smaller than 20 ppm on this surface.

With reference to vector expression in FIG. 7, one of eigen-distribution functions is selected. In FIG. 7, a mark "x" corresponds to the individual eigen-mode, and a mark "○" corresponds to the selected eigen-mode 15. Eigen-modes not marked with "○" are not-selected eigen-mode 16. The selection is done by the method mentioned earlier. When the distribution function to be corrected is selected, an attainable homogeneity can be calculated for prediction by subtracting the error magnetic field component from the measured error magnetic field. In FIG. 7, the attainable homogeneity 17 is shown with a mark of an oval.

FIG. 7 shows two charts of spectrum, in which FIG. 7 (a) shows that before shimming and FIG. 7 (b) shows that after shimming. The homogeneity before shimming is 726 ppm, and it is understood that low-numbered error magnetic field components are large in the chart of spectrum. The eigen-modes marked with "○" have orders of which the number is equal to or smaller than 80 and are eigen-modes selected as error magnetic field components having intensities above about low limit of a measurement accuracy. In this example, the attainable homogeneity is predicted at 15.25 ppm when the selected eigen-mode is corrected. A line 22 indicating an upper limit of the order for selecting the eigen-mode is displayed and a line 23 indicating a lower limit of intensity is displayed on the chart of spectrum in FIG. 7, and then the eigen-mode is selected on the chart of spectrum in FIG. 7.

When the attainable homogeneity predicted is insufficient, the selection of the eigen-distribution function is considered again. The number of eigen-distribution functions is adjusted, i.e., upper and lower limits of the number of an eigen-distribution functions selection range and a lower limit of the eigen-mode intensity $C_j$ are adjusted. In addition, there is another option of adjusting a correction ratio of the eigen-distribution functions selected individually.

Another display in the step 19S is used for checking whether shimming is possible in an instruction chart of the iron arrangement volume shown in FIG. 8. A circle in FIG. 8 shows the shim-tray 5 shown in FIG. 5. There are two shim-trays. However, FIG. 8 shows the lower shim-tray. Meshes 7 in the chart are sections arranged on the shim-tray 5 and an address is allocated to each mesh. In FIG. 8, an address is specified with A, B, C, - - - in right-left direction and with 1, 2, 3, - - - in up and down direction. A value in a mesh 7 indicates an iron volume 18 to be arranged on the mesh 7. In FIG. 8, a unit is 0.1 cc. The structure allows an iron piece of about 5 cc to be arranged on a mesh. The displayed volume is sufficiently small, which allows the iron piece to be arranged. During the repeated adjustment, the volume of the iron piece to be handled becomes small gradually. Accordingly, it is displayed with smaller units of $\frac{1}{10}$, $\frac{1}{100}$, and $\frac{1}{1000}$.

In FIG. 8, contour lines 19 are shown in addition to the meshes 7 and iron piece volume 10 at a mesh on the current potential evaluation plane 13 which is obtained by modeling the shim-tray 5. When the current potential contour lines 19 are considered to be in a coil shape, the error magnetic field can be adjusted with a coil having this shape. This is described in the published paper mentioned earlier. The contour line display according to the present invention provides another advantageous effect. The distribution functions obtained by the singular value decomposition require arrangement of the iron piece or a magnetic moment with spreading on the surface. However, the distribution function requires arrangement (or removal) with a most volume around a peak 8 of the contour line and a valley 9 of the contour line. Using these two characteristics, an iron piece arrangement location for the magnetic field adjustment is flexibly considered. If there is no limitation in arrangement or removal, iron volumes inside a current potential contour line 19 closed with the same sign around a peak of the contour line are added, and the added volume is arranged or removed around the peak 8 of the contour line. In addition, if it is impossible to arrange the iron piece because, for example, a supporting member for the shim-tray around the location exists, it is possible to arrange (or remove) the same volume of the iron piece at another part within the same closed contour line region. The peak 8 in FIG. 8 is between lines of L and M and lines of 7 and 8. On the meshes around a cross part of lines L and M with the lines of 7 and 8, a total volume of 5+3+2+1=11 is required to be arranged. Then, according to the present invention, it is good that the iron piece of the volume of 11 is arranged at the peak 8 of the contour lines at a cross of the lines between L and M with the line between 7 and 8. Such an arrangement reduces a work quantity and provides relaxation in the arrangement position accuracy with facilitation of the work process.

Figure 9:
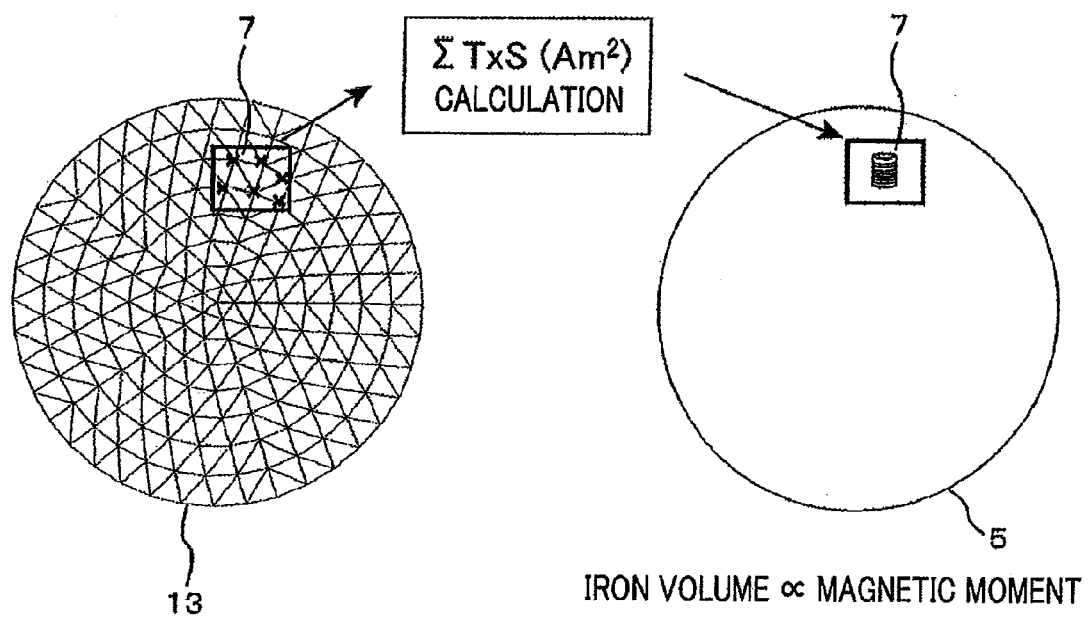
FIG. 9 illustrates an idea of a magnetic moment calculation and an iron volume conversion within a mesh for displaying an iron piece, according to the present invention.

With reference to FIG. 9, will be described a method of calculating the magnetic moment or the iron volume within the mesh. FIG. 9 shows concept of conversion from a node potential value to a magnetic moment from a node potential value into the magnetic moment, and the iron volume. It has already been described that the volume of the iron piece is proportion to the magnetic moment at the description following Eq. (7). In addition, it can be understood that the current potential represents the magnetic moment per a unit area. Then, to obtain a volume of the iron piece at a region, the current potential T is subjected to surface integration in the region. The result is considered as a magnetic moment necessary at the region and is converted into the iron volume as mentioned earlier. FIG. 9 schematically shows a relation between the mesh 7 and a node shown in FIG. 8. A point indicated by "x" is the node. Because they are not continuous functions, for example, a product of a node and areas corresponding to the node are added as shown by an equation in FIG. 9 and is assumed as the magnetic moment. There is a method of obtaining an area corresponding to the node by that an element belonging to the node area corresponding to the node is divided into $\frac{1}{3}$ (in the case of A element).

A comment is made on a dimension of the mesh 7 and an element size on calculation. Regarding a size of the mesh 7, a fineness is required which has a resolution capable of showing the iron piece arrangement distribution shown in FIG. 8. A contour line distribution near an upper limit of the order of the eigen-mode necessary to obtain homogeneity is confirmed to make the size smaller than sizes of the peak and the valley. On the other hand, making the size of the mesh small requires more processes. In FIG. 8, the size is approximately the same as a minimum size of the peak 8 of the contour line and the valley 9 of the contour line. Because the sizes are approximately the same, at a part where the contour lines are fine, there may be a place having an insufficient resolution only with the meshes 7. In this case, the iron piece is arranged with adjusting a place to which the iron piece is arranged with reference to the peaks and valleys of the contour lines. A size of finite elements is determined by the number of the nodes within a mesh. As previously mentioned, an accuracy of the iron piece arrangement volume is approximately $\frac{1}{10}$, and the homogeneity is increased by repeating. When the number of the nodes is equal to or greater than five, even if an error occurs in the corresponding areas, it is considered that a sufficient accuracy is provided. In the example in FIG. 8, there are about 1500 nodes on one side. In a case that there are two current evaluation planes of the upper and lower shim-tray as shown in FIG. 6, it is considered that the total is about 3000 nodes or more.

In this example, the work process moves to an iron piece arrangement work process step 22S because it is predicted that the shimming can be sufficiently done through confirmation of the iron volume display in FIG. 7 (a) and FIG. 8. The prediction is based on that the attainable homogeneity 17 is sufficiently better than the target value and the arranged iron piece has a possible volume.

When it is determined that the attainable homogeneity or the volume of the iron piece is improper in a step 20S of determining whether the shimming is possible or not, the work process returns to the eigen-mode selection and the target determining step 17S again. However, even if various conditions are changed, when it is determined that the magnetic field adjustment is impossible in the magnetic field adjustment possibility determining step 21S of determining whether the magnetic field adjustment to the target is possible or not, the magnet is poor, and the work process advances to a repair and adjustment step 41S.

FIG. 7 (b) shows a spectrum when the shimming is completed. Shimming reaches a homogeneity of 17 ppm. This has not so large difference from the originally predicted value of 15 ppm, so that the prediction of the homogeneity was done at a good accuracy. During reaching the homogeneity of the spectrum in FIG. 7 (a), the repeated work process is done as shown by the flowchart in FIG. 1. The necessity of repeated work process has been described. However, this will be described with an actual example.

The magnetic field adjustment possibility is determined in the step 21S. The content will be described. There may be a case where a sufficient homogeneity cannot be obtained with an appropriate adjustment volume (shimming iron volume) even if the eigen-mode selection is considered again by returning to the step 17S via the step 21S. More specifically, this is because a manufacturing accuracy of the magnet is insufficient, so that the magnetic field is improper, and if it is tried to obtain the target homogeneity, a large volume of the iron piece should be arranged, which is actually impossible. This evaluation provides detection of poorness of the magnetic field without conducting the magnetic field adjustment. When the magnetic field is poor, an appropriate repair is done. From a distribution of the adjustment volume a problematic place can be estimated. In addition, if the repair is impossible, it can be determined that the product is poor. Accordingly, the present invention provides an advantageous effect in that the determination can be provided in which hand is used by repeating the magnetic field adjustment.

When the prediction shows a sufficient attainable homogeneity, an iron piece distribution calculation result necessary for the adjustment is outputted as an enlarged display on a print on paper or by projection, the work process of arranging the iron piece for shimming is carried out in accordance with the distribution. In the iron volume arranged by the shimming work process, there is an error in conversion from the current potential to the iron piece because the volume and a position have errors and a degree of magnetizing of the iron piece depends on a characteristic of material of the iron piece and a distribution of magnetic field within the magnet. Accordingly, one-time work process cannot reach the attainable homogeneity. Therefore, the work process is repeated as shown in FIG. 1 to make the magnetic field closer to a homogeneous state.

Second Embodiment

Figure 10:
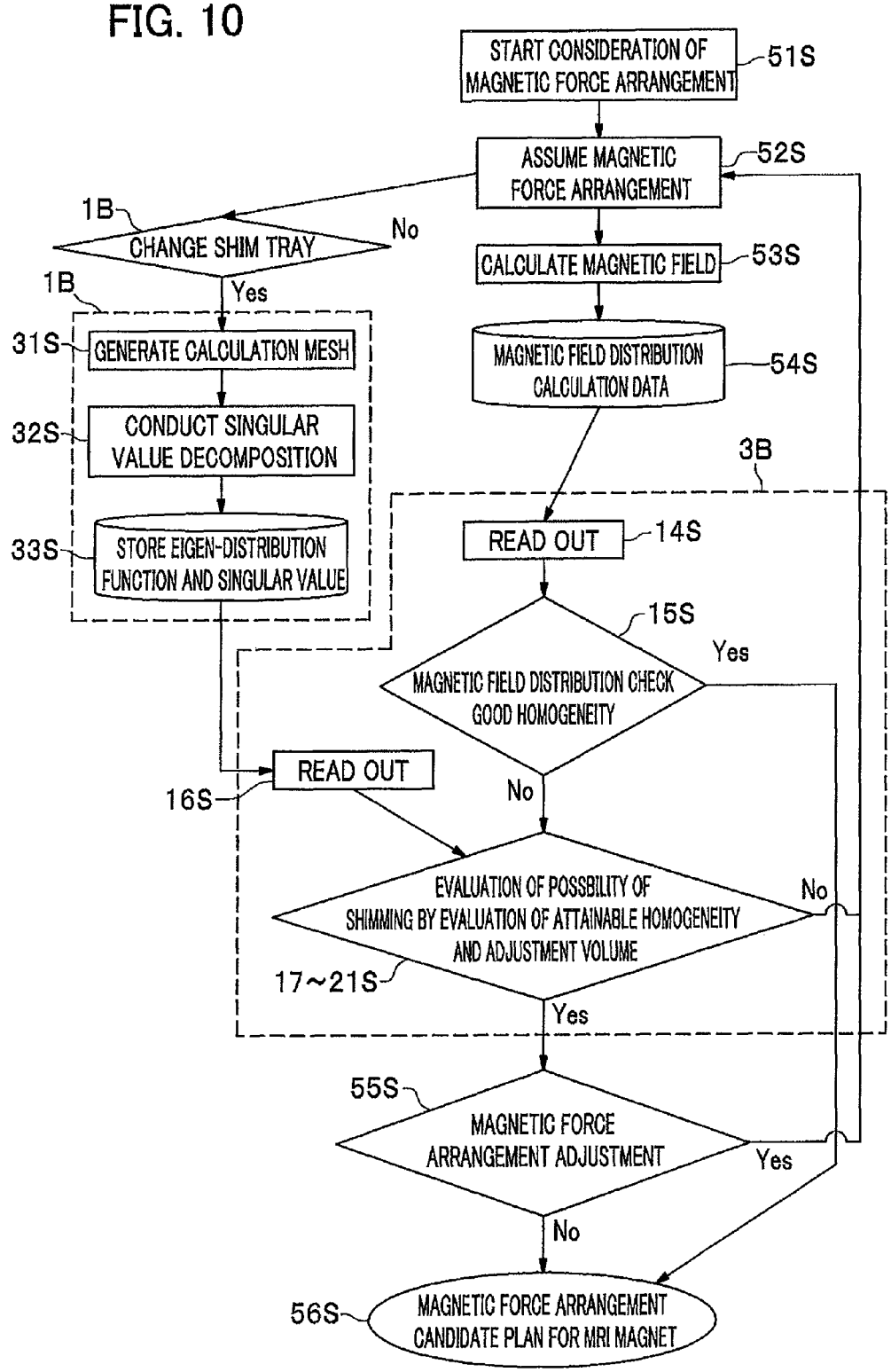
FIG. 10 is a flowchart in a case where the present invention is used in a magnet motive force arrangement designing method.

Will be described a second embodiment. It has been described previously that this method is usable for inspection of quality after manufacturing. However, this method is also usable for designing a magnet in accordance with the same determination. A flowchart of this case is shown in FIG. 10. In this embodiment, the magnetic adjustment is done through calculation, this method is applied to a magnetic force arrangement design by confirming that the target magnetic field accuracy can be reached. After a magnet motive force arrangement consideration start step 51S, a magnet motive force arrangement assuming step 52S is done. A magnetic field calculation step 53S is done on the basis of the magnet motive force arrangement. In addition, a singular value decomposition is done on the basis of the arrangement in the shimming tray from the magnet motive force arrangement. This pre-calculation part 1B is the same as that of the first embodiment. The part 1B is conducted only in a case where it is determined that the shim-tray change is necessary in the magnetic force arrangement improvement determination step 56S on the basis of the magnetic force arrangement assuming step 52S. The pre-calculation part 1B is similar to that in FIG. 1. It is determined whether existing singular value decomposition data can be used in the step 56S. In accordance with the result, only the step 16S reading out the data set of the singular value decomposition result is performed.

The magnetic field data reading step 14S for reading out the magnetic calculation result and a step 15S of determining that the magnetic field homogeneity is good are conducted. When the homogeneity has reached a good value, a magnet motive force arrangement candidate plan for an MRI magnet step 56S is conducted. Generally, it is determined whether the homogeneity becomes good by shimming through the method of the present invention that has been described from the magnetic field distribution. When the homogeneity cannot be sufficiently improved by shimming, or when it is determined that shimming is impossible because the iron volume necessary for shimming is excessive. This determination part 3B is the same steps of 17 to 21S in FIG. 1. The magnetic field adjustment calculation part 3B is the same as that denoted with 3B in FIG. 1.

When shimming is possible, it is considered whether it can be improved by conducting the magnet motive force arrangement adjustment in the step 55S with reference to the iron volume necessary for shimming and a structural design of the whole of the magnet. When the reconsideration of the magnet motive force arrangement is not done, the magnet motive force arrangement candidate plan for an MRI magnet step 56S is done. In addition, when the magnet motive force arrangement is corrected, the work process returns to the magnet motive force arrangement assuming step 52S. When the magnet motive force arrangement is considered again, it can be considered that this may occur in, for example, a case where a magnetic field on the superconducting coil is too excessive, or a case where the electromagnet force causes a difficulty in a supporting mechanism.

As mentioned above, the shimming according to the present invention is virtually done thorough calculation to obtain a candidate of the magnetic force arrangement. In designing the magnet motive force arrangement, for a magnet motive force arrangement of which homogeneity is determined to be sufficient, an entire design such as a magnetic motive force quantity, an electromagnetic force, and a stress, is conducted to determine whether the magnet is successfully formed. When it is difficult to successfully form the magnet, the design is restarted from the step of assuming the magnet motive force arrangement again.

In FIG. 1, as a magnetic field adjusting means, a method of using the magnetic moment by the magnetized ion piece 4 is described as the iron piece arrangement work process step 22S. However, as described in FIG. 3, the magnetized iron piece is equivalent to a current in the small coil 3 as described in FIG. 3. Then, small coils are arranged in meshes in FIG. 8 and it is possible to adjust the current 1 in accordance with the magnetic moment distribution calculated in the method as a replacement of the iron piece arrangement work process step 22S.

In the method of the present invention, there may be a case where a magnetic field adjustment requiring a negative volume may be required. When the magnetic field adjustment is done by current adjustment by the small coil, it can be done by changing a polarity, and when a permanent magnet is used, it can be done by changing a direction. However, magnetization of the iron piece is determined by a peripheral magnetic field circumstance, and the polarity cannot be changed. The negative quantity in this case is considered as follows:

When the selection was made up to a high-numbered part, a part of negative quantity is not arranged. Arrangement of only positive volume part makes a roughness vibration spatial wavelength of the error magnetic field approximately a half, so that the number of eigen-mode order of the error magnetic components that cannot be cancelled as a result of no arrangement of the negative volume shifts to a high-number side of which the number of order is approximately twice the original. Accordingly, the magnetic field intensity decreases and thus can be neglected in magnetic field adjustment. However, when the magnetic field adjustment is done in which relatively-low-numbered eigen-modes are selected, a demand for the negative volume can be generally adjusted by a method of reducing the volume of the iron pieces that have been already arranged in the adjustment up to the high-numbered magnetic field adjustment. However, occasionally, when the volume of the iron pieces in a mesh has been already zero, the iron pieces are removed from the vicinity thereof. The "vicinity" means that a region of closed contour line. Nevertheless, if there is no iron piece to be removed, a specific eigen-mode is intentionally removed from magnitudes necessary for correction to eliminate negative volume. Selecting the specific eigen-mode from high-numbered modes makes affection on the magnetic field small.

In the embodiments shown in FIG. 1] or 10, making the magnetic field adjustment calculation part 3B as software provides a support tool for magnetic field adjustment with a mobility by use with stored data of singular value decomposition result.

Third Embodiment

The first and second embodiments have been described with examples in which the iron pieces are arranged with volumes for generating necessary magnetic moments. However, as described previously, there may be a case where the volume of the iron piece that can be removed in the mesh 7 is insufficient or zero, when a negative volume is required as a volume of iron to be arranged. When a sufficient homogeneity becomes sufficient though control was made as mentioned above, the permanent magnet 4P or a current loop 4C is used instead of the iron piece. These have no problem when being used for the positive iron volume. However, when control can be done by magnetization of iron, it is desirable to use the iron piece that can provide shimming at a low cost.

Figure 11:
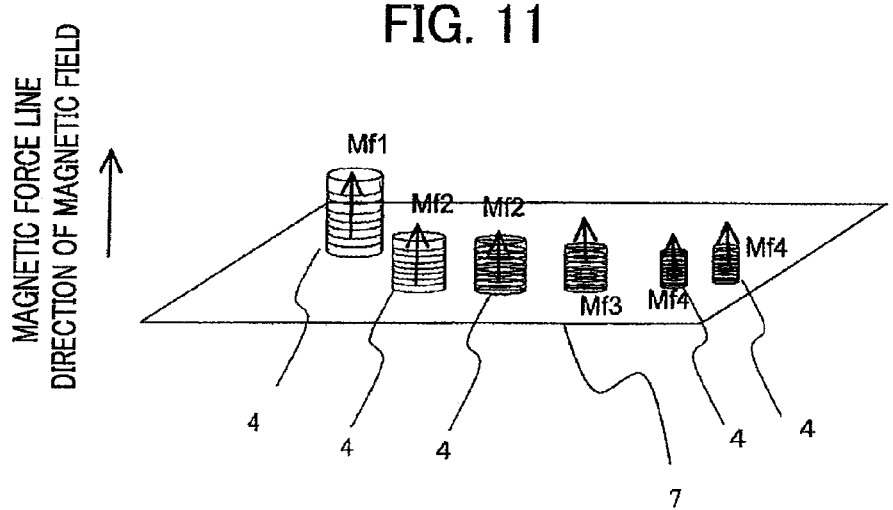
FIG. 11 is an illustration of a shim-tray in which shimming is done with iron pieces.

A status within the meshes in actual shimming will be described as the embodiments. As shown in FIG. 11, it is assumed that iron pieces 4 having several different volumes are arranged also in the first and second embodiments. Magnitudes of the magnetic moments are different among Mf1 to Mf4. The necessary magnetic moments shown in FIG. 9 are given for each MFi by Eq. (13). A volume of iron within a frame is adjusted by combining different volume iron pieces to generate the magnetic moment obtained from Eq. (13).

[Formula 11]

$$Mfi = \Sigma Ti \times Si (Am^2) \qquad (13)$$

In Eq. (13), Ti is a current potential value (A) of a node i within the frame, and Si is an area to which the node belongs. Because the node belongs to a plurality of elements, there is no problem if it is considered that one third of each element belongs to each node in the triangle element shown here. The method of conversion between the volume of the iron piece and the magnetic moment has been argued regarding FIG. 3. However, the magnetic moment of a saturated iron piece can be converted to be approximately 170 Acm²/cc per 1 cc. The magnetic moment necessary for the mesh is converted into the volume of the iron piece to arrange the necessary volume within the mesh. When the magnetic field is weak and thus, the iron piece is not saturated in magnetization, a magnetization M has a different conversion coefficient differently from the saturated magnetization. However, in this case it is determined with reference to a magnetization curve of the material (M-H curve, where M=magnetization intensity T, and H=a magnetic field intensity (A/m or T).

Next, will be described an embodiment of the permanent magnet 4P and the current loop 4C.

Figure 12:
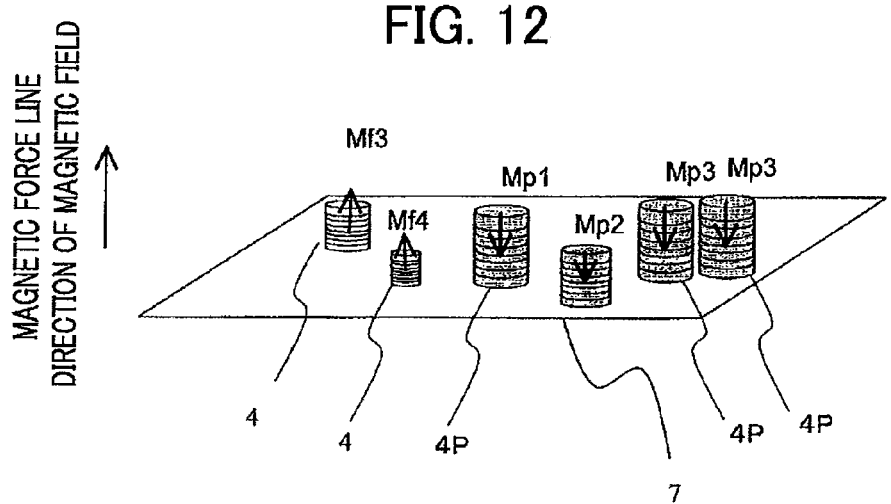
FIG. 12 is an illustration of the shim-tray in which shimming is done with permanent magnets.

When the permanent magnet 4P is used, there is only a different point from the iron piece 4 is in the method of conversion. As shown in FIG. 12, the permanent magnet 4P can arrange a magnetic moment Mp if the magnetic field has a direction opposite to those of its periphery. In other words, the negative iron volume can be arranged. Accordingly, positive and negative volumes can be arranged in a direction or an opposite direction of the magnetic field to meet a direction of Mp to a sign of the necessary volume. The conversion between the magnetic moment and the volume is read from the M-H curve. More specifically, when the permanent magnet is arranged in an opposite direction, the magnetization M is read out from the magnetic field H at the location of arrangement. If the magnetization can be read, the conversion is possible by a method which is the same as that for magnetization of iron described above. A necessary of the permanent magnet is approximately given by Eq. (14). In Eq. (14), the magnetization M may be negative.

[Formula 12]

$$\text{Volume of permanent magnet (cc)}=2.1(\text{necessary magnetic moment})/(170M) \qquad (14)$$

Figure 13:
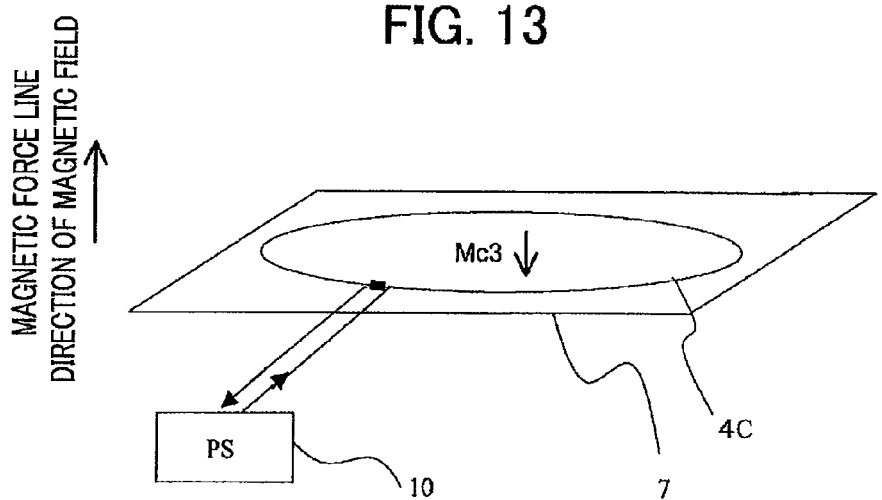
FIG. 13 is an illustration showing a magnetic moment adjustment method by a current loop.

In the current loop shown in FIG. 13, if it is assumed that an area within the loop is S1 on the basis of a principle equation, the magnetic moment Mc is given by Eq. (15).

[Formula 13]

$$Mc = \text{current} \times S1 \qquad (15)$$

A current from a power source 10 is adjusted in consideration of a sign so as to make the magnetic moment equal to the necessary magnetic moment.

The method of generating the magnetic moment and materials actually used in shimming are shown in FIGS. 11, 12, and 13. However, another ferromagnetic material may be possible such as nickel or cobalt in addition to this. In this case, a conversion magnetic moment is obtained by checking the magnetization curve as described regarding the permanent magnet, and then the necessary volume is obtained, and a necessary volume is obtained to arrange the permanent magnet similarly to FIGS. 11 and 12.

There may be a case where the magnetization cannot be obtained from the magnetization curve. For example, there may be a case where a ferromagnetic material for shimming may be different from the original magnetic field. In this case, it is desirable to measure a degree of magnetization of the ferromagnetic material. For example, before and after the arrangement of the ferromagnetic material piece of which magnetization is unclear, a peripheral magnetic field is measured and compared with a magnetic field change in a case where the magnetization is known. Alternatively, it is compared with a magnetic field variation calculated. In addition, if the magnetization curves are those of known materials, a precise non-liner magnetic field calculation is conducted and the calculation results are utilized as magnetization calculation values of the arranged iron pieces 4.

According to the first to third embodiments, a surer magnetic field adjustment is provided by repeating measurement, adjusting iron piece arrangement calculation, and arranging with conformation of a quality of the magnet and with automatically correcting an error in which the final attainable homogeneity is predicted. In addition, this is usable for the magnet force arrangement designing in which a high magnetic field accuracy is required.

INDUSTRIAL APPLICABILITY

The present invention provides a method and an apparatus for adjusting the magnetic field to have a desired magnetic field distribution in the magnet apparatus for generating the magnetic field by arranging the ferromagnetic material such as a coil or iron in nuclear magnetic resonance apparatus (MRI) for medical diagnosis. Particularly, in a nuclear resonance application apparatus such as the MRI, the present invention provides the method and apparatus for homogenization in the measurement region with an extreme high accuracy. Particularly, in the shimming work process in which the error magnetic field is corrected by arrangements of the iron piece, the error magnetic field distribution and the iron piece arrangement distribution are corrected to the homogeneity magnetic field distribution with a combination of respective orthogonal basis.

EXPLANATION OF REFERENCE NUMERALS

1 current
2 magnetization current
3 small coil
4 iron piece
4P permanent magnet
4C current loop
5 shim-tray
6 magnetic field measurement evaluation region
7 mesh
8 peak of contour line
9 valley of contour line
10 DC power supply
11 node
12 finite element
13 current potential evaluation plane
14 set of magnetic field measurement evaluation node
15 selected eigen-mode
16 non-selected eigen-mode
17 attainable homogeneity
18 iron volume arranged in mesh
19 current potential contour line
21 current by current potential
22 line indicating upper limit of a number of order of eigen-mode selection
23 line indicating lower limit of order of eigen-mode selection
1B pre-calculation part
2B magnetic field measurement part
3B magnetic field adjustment calculation part
11S magnetic field adjustment start step
12S magnetic field measurement step
13S measured magnetic field storing step
14S magnetic field data reading step
15S homogeneity determination step
16S singular value decomposition result reading step
17S step of eigen-mode selection and target magnetic field determination
18S calculation step of eigen-mode intensity, correction current potential, iron volume, correction magnetic field distribution, and attainable homogeneity
19S calculation step of spectrum, attainable homogeneity, and iron piece arrangement
20S determination step of possibility in shimming
21S magnetic field adjustment possibility determining step
22S iron piece arrangement work process step
31S calculation mesh generation step
32S singular value decomposition calculation step
33S singular value decomposition result storing step
40S magnetic field adjustment completion step
41S repair and adjustment step
51S magnet motive force arrangement consideration start step
52S magnet motive force arrangement assuming step
53S magnetic field calculation step
54S magnetic field calculation storing step
55S shim-tray change necessity determination step
56S magnetic force arrangement improvement necessity determination step

The invention claimed is:

1. A magnetic field adjustment method of reducing an error magnetic component in a region of a magnetic field generated by either: a magnetic field generation device, a superconducting magnet apparatus, a nuclear magnetic resonance tomographic apparatus, or an apparatus performing magnetic resonance imaging with the magnetic field adjustment method comprising:
measuring a magnetic field distribution of the magnetic field generated by the magnetic field generation device at a plurality of nodes on a predetermined surface;
calculating an error magnetic field that is represented by a difference from the measured magnetic field distribution and a target magnetic field distribution;
selecting one or more eigen-distribution functions from among a plurality of eigen-distribution functions that are obtained by singular value decomposition;
obtaining a current potential distribution on a magnetic field adjustment mechanism in order to approximately correct the error magnetic field according to the selected eigen-distribution functions;
converting the obtained current potential distribution into magnetic moments at the nodes; and
arranging at least one of:
a current loop,
a ferromagnetic piece that is passively magnetized, or
a permanent magnet that is not dependent on an external magnetic field, in accordance with the magnetic moments of the magnetic field adjustment mechanism,
wherein the field adjustment mechanism, which adjusts the generated magnetic field, in order to reduce an error magnetic component in a region of a generated magnetic field, is in a shape of either a curved surface, or a flat surface configured for arranging either the current loop, the ferromagnetic piece or the permanent magnet.

2. The magnetic field adjustment method as claimed in claim 1, further comprising:
calculating correction magnetic field quantities from the current potential distribution;

measuring a residual error magnetic field from the target magnetic field and a magnetic field generated by either the magnetic field generation device, a superconducting magnet apparatus, a nuclear magnetic resonance tomographic apparatus, or an apparatus performing magnetic resonance imaging after arranging at least one of the current loop, the permanent magnet, or the ferromagnetic piece(s) in accordance with the magnetic moments of the magnetic field adjustment mechanism;

checking the appropriateness of the selected Eigen-distribution function; and selecting another Eigen-distribution function based on the residual error magnetic field.

3. The magnetic field adjustment method as claimed in claim 2,
wherein the magnetic field distribution is calculated where a target magnetic field distribution is given, and
when the selected Eigen-distribution is not appropriate, the arrangement of the magnetic field adjustment mechanism is changed until the magnetic field adjustment becomes one that is possible to obtain as an arrangement approximating the target magnetic field.

4. The magnetic field adjustment method as claimed in claim 1, wherein
the current potential distribution is converted into an iron volume density as a quantity proportional to the magnetic moments, and
one or more of the ferromagnetic pieces, or one or more of the permanent magnets is/are arranged in accordance with the converted current potential distribution.

5. The magnetic field adjustment method as claimed in claim 1, wherein selection of the Eigen-distribution functions for obtaining the current potential distribution is made with an order numbered in accordance with a magnitude order of singular values on a spectrum chart of Eigen-distribution intensity, that is included in the error magnetic field.

6. The magnetic field adjustment method as claimed in claim 1, further comprising: displaying contour lines on the magnetic field adjustment mechanism as a density distribution of the current potential distribution, or as magnitudes of the magnetic moments, or as volumes of the ferromagnetic pieces, or as a magnetic intensity of one or more permanent magnets.

7. The magnetic field adjustment method as claimed in claim 6,
wherein the contour lines as well as the magnetic field adjustment mechanism are divided into polygons, and
a magnitude of the magnetic moments, or the volumes of the ferromagnetic pieces, or a magnetic intensity of one or more permanent magnets, are displayed in divided regions with an area integration value, either together with the contour lines, or without the contour lines.

8. The magnetic field adjustment method as claimed in claim 6,
wherein peaks or valleys indicated with contour lines are collectively integrated, and
volumes thereof are arranged at one place, or dispersed at a plurality of places, within the respective peak or valley.

9. The magnetic field adjustment method as claimed in claim 2, further comprising:
repeatedly selecting Eigen-distribution functions until the generated magnetic field is sufficiently homogenous.

10. The magnetic field adjustment method as claimed in claim 9, wherein the generated magnetic field is determined to be sufficiently homogenous, based on a magnitude of the error magnetic field.

11. The magnetic field adjustment method as claimed in claim 2, wherein
selection of the Eigen-distribution functions in order to obtain the current potential distribution is made with an order numbered in accordance with a magnitude order of singular values on a spectrum chart of Eigen-distribution intensity, that is included in the error magnetic field, and the method further comprising:
displaying contour lines on the magnetic field adjustment mechanism as either: a density distribution of the current potential distribution, or magnitudes of the magnetic moments, volumes of one or more ferromagnetic pieces, or a magnetic intensity of at least one permanent magnet are,
wherein a representative value of the residual error magnetic field,
such as a) a value obtained by dividing a difference between a maximum value and a minimum value by a target; or
b) an average magnetic field intensity, is then displayed together, with either: a the spectrum chart, the volume of one or more ferromagnetic pieces, a magnetic intensity of at least one permanent magnet, or a size of the current loops, and arranged on the magnetic field adjustment mechanism.

12. The magnetic field adjustment method as claimed in claim 2, further comprising:
displaying contour lines on the magnetic field adjustment mechanism as either: a density distribution of the current potential distribution, or magnitudes of the magnetic moments, or volumes of one or more ferromagnetic pieces, or a magnetic intensity of permanent magnets.

13. The magnetic field adjustment method as claimed in claim 2, wherein
the magnetic field distribution is calculated where a target magnetic field distribution is given, and
when the selected Eigen-distribution is not appropriate, the arrangement of the magnetic field adjustment mechanism is changed until the magnetic field adjustment becomes one that is possible to obtain as an arrangement approximating the target magnetic field.

14. An apparatus configured for reducing an error magnetic component in a region of a magnetic field comprising:
a magnetic field generating mechanism, by either: a magnetic field generation device, a superconducting magnet apparatus, a nuclear magnetic resonance tomographic apparatus, or an apparatus performing magnetic resonance imaging with which generates the magnetic field;
a magnetic field adjustment mechanism in order to adjust the magnetic field, and which is either: a curved surface, or a flat surface that is configured for arranging a current loop, a ferromagnetic piece that is passively magnetized, or a permanent magnet, that is not dependent on an external magnetic field; and
a computer configured to perform a magnetic field adjustment process including the steps of:
measuring the magnetic field generated by either the magnetic field generation device, a superconducting magnet apparatus, a nuclear magnetic resonance tomographic apparatus, or an apparatus performing magnetic resonance imaging and measuring a plurality of nodes on a predetermined surface;
calculating an error magnetic field that is a difference from the measured magnetic field and a target magnetic field;

selecting one or more Eigen-distribution functions from among a plurality of Eigen-distribution functions that are obtained by singular value decomposition;

obtaining a current potential distribution on a magnetic field adjustment mechanism in order to approximately correct the error magnetic field, according to the selected Eigen-distribution functions;

converting the current potential distribution into magnetic moments at the nodes; and determining an arrangement of at least one of a current loop, a permanent magnet, or a ferromagnetic piece in accordance with the magnetic moments of the magnetic field adjustment mechanism.

15. The apparatus as claimed in claim 14, wherein the magnetic field adjustment process further includes:

calculating correction magnetic field quantities from the current potential distribution, measuring a residual error magnetic field from the target magnetic field and the magnetic field generated by either the magnetic field generation device, a superconducting magnet apparatus, a nuclear magnetic resonance tomographic apparatus, or an apparatus performing magnetic resonance imaging after arranging at least one of the current loop, the permanent magnet, or the ferromagnetic piece that corresponds to the magnetic moments of the magnetic field adjustment mechanism, checking the appropriateness of the selected Eigen-distribution function, and selecting another Eigen-distribution function based on the residual error magnetic field.

16. The apparatus as claimed in claim 15, further comprising:

a display, in order to show contour lines on the magnetic field adjustment mechanism as: a density distribution of the current potential distribution, or magnitudes of the magnetic moments, volumes of the ferromagnetic pieces, or volumes of the permanent magnets.

17. The apparatus as claimed in claim 14, wherein the current potential distribution is converted into an iron volume density as a quantity proportional to the magnetic moments, and the ferromagnetic piece or the permanent magnet, and are then arranged in accordance with the converted current potential distribution.

18. The apparatus as claimed in claim 14, wherein selection of the Eigen-distribution functions in order to obtain a current potential distribution is made with an order numbered in accordance with a magnitude order of singular values on a spectrum chart of Eigen-distribution intensity, that is included in the error magnetic field.

19. The apparatus as claimed in claim 14, further comprising: a display, in order to show contour lines on the magnetic field adjustment mechanism as a density distribution of the current potential distribution, or magnitudes of the magnetic moments, or a volume of the ferromagnetic piece or as a magnetic intensity of the permanent magnet.

20. The apparatus as claimed in claim 14, wherein the contour lines as well as the magnetic field adjustment mechanism are divided into polygons, and a magnitude of the magnetic moments, or the volume of the ferromagnetic piece or a magnetic intensity of the permanent magnet are displayed in divided regions with an area integration value, either together with the contour lines, or without the contour lines.

21. The apparatus as claimed in claim 19, wherein peaks or valleys indicated with contour lines are collectively integrated, and volumes thereof is arranged at one place, or dispersed at a plurality of places, within the respective peak or valley.

22. The apparatus as claimed in claim 14, wherein the magnetic field adjustment process further includes:

repeatedly selecting Eigen-distribution functions until the generated magnetic field is sufficiently homogenous.

23. The apparatus as claimed in claim 22, wherein the generated magnetic field is determined to be sufficiently homogenous, based on a magnitude of the error magnetic field.

24. The apparatus as claimed in claim 15, wherein selection of the Eigen-distribution functions in order to obtain the current potential distribution is made with an order numbered in accordance with a magnitude order of singular values on a spectrum chart of Eigen-distribution intensity, included in the error magnetic field, the apparatus further comprising:

a display, in order to show contour lines on the magnetic field adjustment mechanism as a density distribution of the current potential distribution, or magnitudes of the magnetic moments, a volume of the ferromagnetic piece, or a magnetic intensity of the permanent magnet, and wherein a representative value of the residual error magnetic field, such as a) a value obtained by dividing a difference between a maximum value and a minimum value by a target; or b) an average magnetic field intensity is then displayed together, with either: the spectrum chart, the volume of the ferromagnetic piece, the magnetic intensity of the permanent magnet, or a size of the current loop arranged in the magnetic adjustment process.

* * * * *